United States Patent

Iwasaki et al.

[11] Patent Number: 6,048,892
[45] Date of Patent: Apr. 11, 2000

[54] ESTER COMPOUND PESTICIDE CONTAINING THEREOF

[75] Inventors: Tomonori Iwasaki, Sanda; Masayo Sugano, Osaka, both of Japan

[73] Assignee: Sumitomo Chemical Company, Limited, Osaka, Japan

[21] Appl. No.: 09/320,212

[22] Filed: May 26, 1999

Related U.S. Application Data

[63] Continuation-in-part of application No. 09/182,889, Oct. 30, 1998, abandoned, which is a continuation of application No. 09/000,950, Dec. 30, 1997, abandoned, and a continuation-in-part of application No. 09/136,456, Aug. 19, 1999, which is a continuation of application No. 09/000,951, Dec. 30, 1997, abandoned.

[51] Int. Cl.[7] .......................... A01N 43/08; C07D 307/02
[52] U.S. Cl. ............................. 514/461; 549/499
[58] Field of Search ............... 549/499; 514/461

[56] References Cited

U.S. PATENT DOCUMENTS

| | | | |
|---|---|---|---|
| 4,482,570 | 11/1984 | Piccardi et al. | 424/304 |
| 5,405,865 | 4/1995 | Benoit et al. | 514/438 |
| 5,591,727 | 1/1997 | Bencrits | 514/461 |

FOREIGN PATENT DOCUMENTS

| | | |
|---|---|---|
| 0003336 | 6/1979 | European Pat. Off. . |
| 6183102 | 4/1986 | Japan . |
| 383904 | 4/1991 | Japan . |
| 4208202 | 7/1992 | Japan . |
| 6211611 | 2/1994 | Japan . |
| 1133554 | 11/1968 | United Kingdom . |

OTHER PUBLICATIONS

Bull. Chem. Soc. Jpn., (1987), vol. 60, No. 12, pp. 4385–4394.
EPO Search Report dated Mar. 3, 1999.
Claim of EP Application No. 98117919.5.
Database WPI, Section Ch, Week 9435, Derwent Publications Ltd., XP002093576.
Chemical Abstracts, vol. 066, No. 19, May 8, 1967, XP002093575.

*Primary Examiner*—Amelia Owens
*Attorney, Agent, or Firm*—Stevens, Davis, Miller & Mosher, L.L.P.

[57] ABSTRACT

Ester compounds represented by the following formula (I)

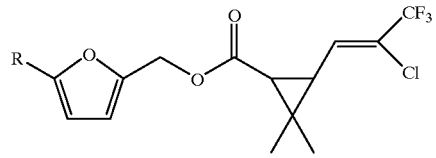

wherein R is a methyl, ethyl, n-propyl or allyl group, have excellent effects on the control of harmful pests, and they are, therefore, useful as the active ingredients of pesticides.

15 Claims, No Drawings

ESTER COMPOUND PESTICIDE CONTAINING THEREOF

CROSS REFERENCE TO RELATED APPLICATIONS

This application is a continuation-in-part of U.S. Ser. No. 09/182,889, filed Oct. 30, 1998 now abandoned; which, in turn, is a continuation of U.S. Ser. No. 09/000,950, filed Dec. 30, 1997, now abandoned; and a continuation-in-part of U.S. Ser. No. 09/136,456, filed Aug. 19, 1999; which, in turn, is a continuation of U.S. Ser. No. 09/000,951, filed Dec. 30, 1997, now abandoned, the disclosures of each of which are herein incorporated in their entirety by reference.

The present invention relates to an ester compound and a pesticide containing the same as an active ingredient.

The object of the present invention is to provide a compound having an excellent effect for controlling noxious pests such as arthropods (including insects, mites, ticks, spiders and so on) and nematodes. As a result, it has been found that an ester compound represented by the following formula (I):

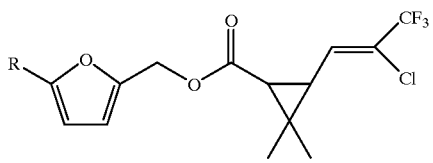

wherein R is a methyl, ethyl, n-propyl or allyl group, has an excellent effect for controlling noxious pests.

That is, the present invention provides an ester compound represented by the above-mentioned formula (I) (hereinafter referred to as a "present compound") and a pesticide containing the same as an active ingredient.

The present compound can be produced, for example, by the process which comprises reacting an alcohol compound represented by the following formula (II):

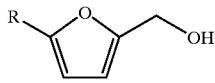

wherein R is as defined above, with a carboxylic acid represented by the following formula (III):

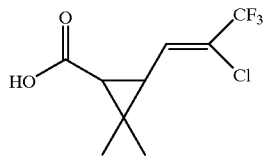

or a reactive derivative thereof.

Examples of the reactive derivative of the carboxylic acid include acid halide compound, acid anhydride compound and the like.

It is preferred that the reaction of the alcohol compound represented by the formula (II) with the carboxylic acid represented by the formula (III) is conducted in an inert solvent in the presence of a suitable condensing agent, if necessary. And it is preferred that the reaction of the alcohol compound represented by the formula (II) with the above-mentioned reactive derivative is conducted in an inert solvent in the presence of a base, if necessary. Examples of the condensing agent include dicyclohexylcarbodiimide (DCC), 1-ethyl-3-(3-dimethylaminopropyl) carbodiimide hydrochloride (WSC) and the like. Examples of the base to be used include organic bases such as triethylamine, pyridine, 4-dimethylaminopyridine, diisopropylethylamine and the like. Examples of the solvent to be used include hydrocarbons such as benzene, toluene, hexane and the like; ethers such as diethyl ether, tetrahydrofuran and the like; and halogenated hydrocarbons such as dichloromethane, 1,2-dichloroethane and the like.

The reaction time is usually within a range from 5 minutes to 72 hours.

The reaction temperature can be preferably within a range from $-20°$ C. to the boiling point of the solvent used for the reaction or $100°$ C., more preferably from $-5°$ C. to the boiling point of the solvent used for the reaction or the temperature up to $100°$ C. The molar ratio of the alcohol compound represented by the formula (II) to the carboxylic acid represented by the formula (III) or the reactive derivative thereof to be used can be optionally set, but is advantageous to set an equimolar ratio or the ratio similar to the equimolar ratio. The condensing agent or base can be used in an amount within a range from an equimolar amount to an excessive amount, preferably from an equimolar amount to 5 mols, based on 1 mol of the alcohol compound of the formula (II).

After the completion of the reaction, the reaction solution can be subjected to a usual work-up treatment such as extraction with organic solvent, concentration, and so on to give the objective present compound. If necessary, it may be purified by usual procedure such as chromatography distillation and/or the like.

The present compounds have stereoisomers, that is optical isomers (R, S) and geometrical isomers (cis/trans and E/Z), and all stereoisomers and a mixture thereof which have an activity for controlling noxious pests are included in the present invention.

In the above production process, the carboxylic acid represented by the formula (III) to be used as the starting material can be prepared, for example, according to the method described in Bull. Chem. Soc. Jpn. 4385–4394 (1987).

In the above production process, the alcohol compounds represented by the formula (II) to be used as another starting material include 5-methyl-2-furufuryl alcohol, 5-ethyl-2-furufuryl alcohol, 5-propyl-2-furufuryl alcohol and 5-allyl-2-furufuryl alcohol, which can be prepared in the usual way.

Examples of noxious pests against which the present compound exhibits a control effect include the following insects, mites and ticks:

Hemiptera:
  Delphacidae (planthoppers) such as *Laodelphax striatellus* (small brown planthopper), *Nilaparvata lugens* (brown planthopper) and *Sogatella furcifera* (whitebacked rice planthopper); Cicadelloidea (leafhoppers) such as *Nephotettix cincticeps* (green rice leafhopper), *Nephotettix virescens* (green rice leafhopper) and *Recilia dorsalis*; Aphidoidea (aphids); stink bugs such as Pentatomidae, Acanthosomatidae, Urostylidae, Dinidoridae, Coreidae and Alydidae; Aleyrodidae (whiteflies); Tingidae (lace bugs); Psyllidae (jumping plantlice); and so on;

Lepidoptera:
  Pyralidae such as *Chilo suppressalis* (rice stem borer), *Cnaphalocrocis medinalis* (rice leafroller) and *Plodia interpunctella* (Indian meal moth); Noctuidae such as Spodoptera litura (tobacco cutworm), *Pseudaletia separata* (rice armyworm), Mamestra brassicae (cabbage armyworm); Pieridae such as *Pieris rapae crucivora* (common cabbageworm); Tortricidae such as Adoxophyes spp.; Carposinidae; Lyonetiidae; Lymantriidae (tussock moths); Plusiinae; Agrotis spp. such as *Agrotis segetum* and *Agrotis ipsilon* (black cutworm); Heliotis spp.; *Plutella xylostella* (diamondback moth); *Tinea pellionella* (casemaking clothes moth); *Tineola bisselliella* (webbing clothes moth); and so on;

Diptera:

Culex spp. such as *Culex pipiens pallens* (common mosquito) and Culex tritaeniorhynchus; Aedes spp. such as *Aedes aegypti* and *Aedes albopictus*; Anopheles spp. such as *Anopheles sinensis*; Chironomidae (midges); Muscidae such as *Musca domestica* (housefly), *Muscina stabulans* (false stablefly) and *Fannia canicularis* (little housefly); Calliphoridae; Sarcophagidae; Anthomyiidae such as *Delia platura* (seedcorn maggot) and *Delia antiqua* (onion maggot); Tephritidae (fluit flies); Drosophilidae; Psychodidae (moth flies); Simuliidae (black flies); Tabanidae; Stomoxyidae; Ceratopogonidae (biting midges); and so on;

Coleoptera (beetles):

Diabrotica spp. (corn rootworms) such as *Diabrotica virgifera* (western corn rootworm) and *Diabrotica undecimpunctata howardi* (southern corn rootworm); Scarabaeidae such as *Anomala cuprea* and *Anomala rufocuprea* (soybeen beetle); Curculionidae such as *Sitophilus zeamais* (maize weevil) and *Lissorhoptrus oryzophilus* (ricewater weevil); Tenebrionidae (darkling beetles) such as *Tenebrio molitor* (yellow mealworm) and *Tribolium castaneum* (red flour beetle); Chrysomelidae such as *Phyllotreta striolata* (striped flea beetle) and *Aulacophora femoralis* (cucurbit leaf beetle); Anobiidae; Epilachna spp. such as *Epilachna vigintioctopunctata* (twentyeight-spotted ladybird); Lyctidae (powder post beetles); Bostrychidae (false powder post beetles); Cerambycidae; *Paederus fuscipes* (robe beetle); and so on;

Dictyoptera:

*Blattella germanica* (German cockroach); *Periplaneta fuliginosa* (smokybrown cockroach); *Periplaneta americana* (American cockroach); *Periplaneta brunnea* (brown cockroach); *Blatta orientalis* (oriental cockroach); and so on;

Thysanoptera

*Thrips palmi*; *Thrips hawaiiensis* (flower thrips); and so on;

Hymenoptera:

Formicidae (ants); Vespidae (hornets); Bethylidae; Tenthredinidae (sawflies) such as *Athalis rosae ruficornis* (cabbage sawfly); and so on;

Orthoptera:

Gryllotalpidae (mole crickets); Acridadae (grasshoppers); and so on;

Siphonaptera:

*Ctenocephalides canis* (dog flea); *Ctenocephalides felis* (cat flea); *Pulex irritans*; and so on;

Anoplura:

*Pediculus humanus capitis*; *Pthirus pubis*; and so on;

Isoptera:

*Reticulitermes speratus*; *Coptotermes formosanus*; and so on;

Tetranychidae:

*Tetranychus cinnabarinus* (carmine spider mite); *Tetranychus urticae* (two-spotted spider mite); *Tetranychus kanzawai* (Kanzawa spider mite); *Panonychus citri* (citrus red mite); *Panonychus ulmi* (European red mite); and so on;

House-dust mites:

Acaridae; Dermatophagoidinae; Pyroglyphinae; Cheyletidae; Macronyssidae such as Ornithonyssus spp.; and so on;

Ticks:

Ixodidae such as Boophilus microplus; and so on.

The present compound to be used as an active ingredient of a pesticide is usually formulated by mixing with a solid carrier, a liquid carrier, a gaseous carrier or bait, or is impregnated with a base material of a mosquito-coil or mosquito-mat for electric heating fumigation.

A surfactant, a sticking agent, a dispersion agent, a stabilizer and other auxiliaries or additives are added if necessary Examples of the formulations for the present compound include oil solutions, emulsifiable concentrates, wettable powders, flowable formulations, granules, dusts, aerosols, combustible or chemical fumigants such as mosquito-coil, mosquito-mats for electric heating fumigation and a porous ceramic fumigant, volatile formulation applied on resin or paper, fogging formulation, ULV formulation (formulations for ultra low volume application) and poisonous bait.

These formulations include the present compound as an active ingredient in an amount of 0.001% to 95% by weight.

Examples of the solid carrier to be used for the formulation include fine powder or granules of clays (e.g. kaolin clay, diatomaceous earth, synthetic hydrated silicon oxide, bentonite, Fubasami clay, acid clay), talc, ceramics, other inorganic minerals (e.g. sericite, quartz, sulfur, active carbon, calcium carbonate, hydrated silicon oxide) and chemical fertilizers (e.g. ammonium sulfate, ammonium phosphate, ammonium nitrate, ammonium chloride and urea).

Examples of the liquid carrier to be used for the formulation include water, alcohols such as methanol and ethanol, ketones such as acetone and methyl ethyl ketone, aromatic hydrocarbons such as benzene, toluene, xylene, ethylbenzene and methylnaphthalene, aliphatic hydrocarbons such as hexane, cyclohexane, kerosine and gas oil, esters such as ethyl acetate and butyl acetate, nitrites such as acetonitrile and isobutyronitrile, ethers such as diisopropyl ether and dioxane, acid amides such as N,N-dimethylformamide and N,N-dimethylacetamide, halogenated hydrocarbons such as dichloromethane, trichloroethane and carbon tetrachloride, dimethyl sulfoxide, vegetable oils such as soybean oil and cottonseed oil.

Examples of the gaseous carrier or propellant to be used for the formulation include chlorofluorocarbons, butane gas, LPG (liquefied petroleum gas), dimethyl ether and carbon dioxide.

Examples of the surfactant include alkyl sulfates, alkylsulfonates, alkylarylsulfonates, alkyl aryl ethers, polyoxyethylenealkyl aryl ethers, polyethylene glycol ethers, polyhydric alcohol ethers and sugar alcohol derivatives.

Examples of the sticking agents, the dispersing agent, and other auxiliaries or additives include casein, gelatin, polysaccharides such as starch, gum arabic, cellulose derivatives and alginic acid, lignin derivatives, bentonite, sugars and synthetic water-soluble polymers such as polyvinyl alcohol, polyvinylpyrrolidone and polyacrylic acid.

Examples of the stabilizer include PAP (acid isopropyl phosphate), BHT (2,6-di-tert-butyl-4-methyphenol), BHA (mixture of 2-tert-butyl-4-methoxyphenol and 3-tert-butyl-4-methoxyphenol), vegetable oils, mineral oils, surfactants, fatty acids and esters of fatty acid.

The base material of the mosquito-coil may be a mixture of raw plant powder such as wood powder and Pyrethrum marc and a binding agent like Tabu powder (powder of *Machilus thunbergii*), starch or gluten.

The base material of the mosquito-mat for electric heating fumigation may be a plate of compacted fibrils of cotton linters or a mixture of pulp and cotton linters.

The base material of the combustible fumigant includes, for example, an exothermic agent such as a nitrate, a nitrite, a guanidine salt, potassium chlorate, nitrocellulose, ethylcellulose and wood powder, a pyrolytic stimulating agent such as an alkali metal salt, an alkaline earth metal salt, a dichromate and chromate, an oxygen source such as potassium nitrate, a combustion assistant such as melanin and wheat starch, a bulk filler such as diatomaceous earth and a binding agent such as synthetic glue.

The base material of the chemical fumigant includes, for example, an exothermic agent such as an alkali metal sulfide, polysulfide, hydrogensufide, hydrated salt and calcium oxide, a catalytic agent such as carbonaneous substance, iron carbide and activated clay, an organic foaming agent such as azodicarbonamide, benzenesulfonylhydrazide, N,N'-dinitrosopentamethylenetetramine, polystyrene and polyurethane and a filler such as natural or synthetic fibers.

Examples of the base material of the volatile agent include thermoplastic resins, filter paper and Japanese paper.

The base material of the poisonous baits includes a bait component such as grain powder, vegetable oil, sugar and crystalline cellulose, an antioxidant such as dibutylhydroxytoluene and nordihydroguaiaretic acid, a substance for preventing erroneous eating such as red pepper powder, an attractant such as cheese flavor onion flavor and peanut oil.

The flowable formulations are usually prepared by finely dispersing the present compound at a ratio of 1 to 75 wt % in water containing a 0.5 to 15 wt % dispersing agent, a 0.1 to 10 wt % suspension assistant (for example, protective colloid or a compound giving thixotropy) and 0 to 10 wt % additives (for example, an antifoamer, a rust preventive agent, a stabilizer, a developing agent, a penetrating assistant, antifreezing agent, a bactericide, a fungicide).

The present compound may be dispersed in oil, in which the present compound is substantially insoluble, to form oil suspensions.

Examples of the protective colloid include gelatin, casein, gums, cellulose ethers and polyvinyl alcohol. The compound giving thixotropy may be bentonite, aluminum magnesium silicate, xanthan gum or polyacrylic acid.

The formulations thus obtained is used as prepared or diluted with water and may be used simultaneously with another insecticide, another acaricide, another nematicide, a repellent, a bactericide, a herbicide, a plant growth regulator, a synergist, a fertilizer or a soil conditioner under non-mixed conditions or pre-mixed conditions.

The synergists are exemplified by piperonyl butoxide, N-(2-ethylhexyl)bicyclo[2.2.1]hept-5-ene-2,3-dicarboximide, N-(2-ethylhexyl)-1-isopropyl-4-methylbicyclo[2.2.1]oct-5-ene-2,3-dicarboximide and 1,1'-oxybis(2,3,3,3-tetrachloropropane). Such a synergist is usually used by 0.2 to 50 weight parts per 1 weight part of the present compound. The combination of the present compound and piperonyl butoxide is especially preferable. The weight ratio of the present compound and piperonyl butoxide is usually 1:0.2 to 1:50, preferably 1:0.5 to 1:25, more preferably 1:1 to 1:20.

Insecticides, acaricides and nematicides to be used together with the present compounds include organophosphorus compounds such as fenitrothion [O,O-dimethyl O-(3-methyl-4-nitrophenyl) phosphorothioate], fenthion [O,O-dimethyl O-[3-methyl-4-(methythio)phenyl] phosphorothioate], Diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], acephate [O,S-dimethyl acetylphosphoramodothioate], methidathion [S-2,3-dihydro-5-methoxy-2-oxo-1,3,4-thiadiazol-3-ylmethyl O,O-dimethyl phosphorodithioate], disulfoton [O,O-diethyl S-2-ethylthioethyl phospborodithioate], DDVP [2,2-dichlorovinyl dimethyl phosphate], suiprofos [O-ethyl O-4-(methylthio)phenyl S-propyl phosphorodithioate], cyanophos [O-4-cyanophenyl O,O-dimethyl phosphorothioate], dioxabenzofos [2-methoxy-4H-1,3,2-benzodioxaphosphorin 2-sulfide], dimethoate [O,O-dimethyl S-methylcarbamoylmethyl phosphorodithioate], phenthoate [ethyl dimethoxyphosphinothioylthio(phenyl)acetate], malathion [1,2-bis(ethoxycarbonyl)ethyl O,O-dimethyl phosphorodithioate], trichlorfon [dimethyl 2,2,2-trichloro-1-hydroxyethylphosphonate], azinphos-methyl [O,O-dimethyl S-[(4-oxo-1,2,3-benzotriazin-3(4H)-yl)methyl] phosphorodithioate], monocrotophos [dimethyl (E)-1-methyl-2-(methylcarbamoyl)vinyl phosphate] and ethion [O,O,O', O'-tetraethyl S,S'-methylene bis (phosphorodithioate)], carbamate compounds such as fenobucarb [2-sec-butylphenyl methylcarbamate], benfracarb [ethyl N-[2,3-dihydro-2,2-dimethylbenzofuran-7-yloxycarbonyl(methyl)aminothio]-N-isopropyl-β-alaninate], propoxur [2-isopropoxyphenyl methylcarbamate], carbosulfan [2,3-dihydro-2,2-dimethylbenzofuran-7-yl (dibuthylaminothio) methylcarbamate], carbaryl [1-naphthyl methylcarbamate], methomyl [S-methyl N-(methylcarbamoyloxy) thioacetimidate], ethiofencarb [2-(ethylthiomethyl)phenyl methylcarbamate], aldicarb [2-methyl-2-(methylthio) propionaldehyde O-methylcarbamoyloxime], oxamyl [N,N-dimethyl-2-methylcarbamoyloxyimino-2-(methylthio) acetamide], fenothiocarb [S-4-phenoxybuthyl dimethylthiocarbamate] and metoxadiazone [5-methoxy-3-(2-methoxyphenyl)-1,3,4-oxadiazol-2(3H)-one], pyrethroid compounds such as etofenprox [2-(4-ethoxyphenyl)-2-methylpropyl 3-phenoxybenzyl ether], fenvalerate [α-cyano-3-phenoxybenzyl 2-(4-chlorophenyl)-3-methylbutyrate], esfenvalerate [(S)-α-cyano-3-phenoxybenzyl (S)-2-(4-chlorophenyl)-3-methylbutyrate], fenpropathrin [α-cyano-3-phenoxybenzyl 2,2,3,3-tetramethylcyclopropanecarboxylate], cypermethrin [α-cyano-3-phenoxybenzyl 3-(2,2-dichlorovinyl)-2,2-dimethylcyclopropanecarboxylate], permethrin [3-phenoxybenzyl 3-(2,2-dichlorovinyl)- 2,2-dimethylcyclopropanecarboxylate], cyhalothrin [α-cyano-3-phenoxybenzyl (Z)-3-(2-chloro-3,3,3-trifluoroprop-1-enyl)-2,2-dimethylcyclopropanecarboxylate], deltamethrin [(S)-α-cyano-3-phenoxybenzyl (1R)-cis-3-(2,2-dibromovinyl)-2,2-dimethylcyclopropanecarboxylate], cyclopvrothrin [α-cyano-3-phenoxybenzyl 2,2-dichloro-1-(4-ethoxyphenyl)cyclopropanecarboxylate], fluvalinate [α-cyano-3-phenoxybenzyl N-(2-chloro-α, α, α-trifluoro-p-tolyl)-D-valinate], bifenthrin [2-methylbiphenyl-3-ylmethyl (Z)-3-(2-chloro-3,3,3-trifluoroprop-1-enyl)-2,2-dimethylcyclopropanecarboxylate], 2-methyl-2-(4-bromodifluoromethoxyphenyl)propyl 3-phenoxybenzyl ether, tralomethrin [(S)-α-cyano-3-phenoxybenzyl (1R,cis)-3-(1,2,2,2-tetrabromoethyl)-2,2- dimethylcyclopropanecarboxylate], silafluofen [(4-ethoxyphenyl) [3-(4-fluoro-3-phenoxyphenyl)propyl] dimethylsilane], d-phenothrin [3-phenoxybenzyl (1R)-chrysanthemate], cyphenothrin [α-cyano-3-phenoxybenzyl (1R)-chrysanthemate], d-resmethrin [5-benzyl-3-furylmethyl (1R)-chrysanthemate], acrinathrin [(S)-α-cyano-3-phenoxybenzyl (Z)-(1R,cis)-2,2-dimethyl-3-[2-(2,2,2-trifluoro-1-trifluoromethylethoxycarbonyl)vinyl] cyclopropanecarboxylate], cyfluthrin [α-cyano-4-fluoro-3-phenoxybenzyl 3-(2,2-dichlorovinyl)-2,2-dimethylcyclopropanecarboxylate], tefluthrin [2,3,5,6-tetrafluoro-4-methylbenzyl (Z)-3-(2-chloro-3,3,3-trifluoroprop-1-enyl)-2,2-dimethylcyclopropanecarboxylate], transfluthrin [2,3,5,6-tetrafluorobenzyl (1R,trans)-3-(2,2-dichlorovinyl)-2,2-dimethylcyclopropanecarboxylate], tetramethrin [3,4,5,6-tetrahydrophthalimidomethyl chrysanthemate], allethrin [3-allyl-2-methyl-4-oxocyclopent-2-enyl chrysanthemate], prallethrin [(S)-2-methyl-4-oxo-3-(2-propynyl)cyclopent-2-enyl (1R)-chrysanthemate], empenthrin [(E)-1-ethynyl-2-methyl-2-pentenyl (1R)-chrysanthemate], imiprothrin [2,5-dioxo-3-(prop-2-ynyl)imidazolidin-1-ylmethyl (1R)-chrysanthemate], d-furamethrin [5-(prop-2-ynyl)furfuryl (1R)-chrysanthemate] and 5-(prop-2-ynyl)furfuryl 2,2,3,3-tetramethylcyclopropane-carboxylate, thiadiazine derivatives such as buprofezin [2-tert-butylimino-3-isopropyl-5-phenyl-1,3,5-thiadiazin-4-one], nitroimidazolidine derivatives, nereistoxin derivatives such as cartap [S,S'-(2-dimethylaminotrimethylene) bis(thiocarbamate)], thiocyclam [N,N-dimethyl-1,2,3-trithian-5-ylamine] and bensultap [S,S'-2-dimethylaminotrimethylene di(benzenethiosulfonate)], N-cyanoamidine derivatives such as N-cyano-N'-methyl-N'-(6-chloro-3-pyridylmethyl) acetamidine, chlorinated hydrocarbons such as endosulfan [6,7,8,9,10,10-hexachloro-1,5,5a,6,9,9a-hexahydro-6,9-methano-2,4,3-benzodioxathiepine 3-oxide], γ-BHC [1,2,3,4,5,6-hexachlorocyclohexane] and dicofol [2,2,2-trichloro-1,1-bis(4-chlorophenyl)ethanol], benzoylphenylurea compounds such as chlorfluazuron [1-[3,5-dichloro-4-(3-chloro-5-trifluoromethyl-2-pyridyloxy)phenyl]-3-(2,6-difluorobenzoyl) urea], teflubenzuron [1-(3,5-dichloro-2,4-difluorophenyl)-3-(2,6-difluorobenzoyl) urea] and flufenoxuron [1-[4-(2-chloro-4-trifluoromethylphenoxy)-2-fluorophenyl]-3-(2,6-difluorobenzoyl)urea], formamidine derivatives such as amitraz [N-methylbis(2,4-xylyliminomethyl)amine] and chlordimeform [N'-(4-chloro-2-methylphenyl)-N,N-dimethylmethanimidamide], thiourea derivatives such as diafenthiuron [1-tert-butyl-3-(2,6-diisopropyl-4-phenoxyphenyl)thiourea], phenylimidazole derivatives, phenylpyrazole derivatives, bromopropylate [isopropyl 4,4'-dibromobenzilate], tetradifon [4-chlorophenyl 2,4,5-trichlorophenyl sulfone], chinomethionat [S,S-(6-methylquinoxaline-2,3-diyl) dithiocarbonate], propargite [2-(4-tert-butylphenoxy) cyclohexyl prop-2-ynyl sulfite], fenbutatin oxide [bis[tris(2-methyl-2-phenylpropyl) tin]oxide], hexythiazox [trans-5-(4-chlorophenyl)-N-cyclohexyl-4-methyl-2-oxo-3-thiazolidincarboxamide], clofentezine [3,6-bis(2-chlorophenyl)-1,2,4,5-tetrazine], pyridaben [2-tert-butyl-5-(4-tert-butylbenzylthio)-4-chloropyridazin-3(2H)-one], fenpyroximate [tert-butyl (E)-α-(1,3-dimethyl-5-phenoxypyrazol-4-ylmethyleneaminooxy)-p-toluate], tebufenpyrad [N-(4-tert-butylbenzyl)-4-chloro-3-ethyl-1-methylpyrazole-5-carboxamide], pyrimidifen [5-chloro-N-[2-[4-(2-ethoxyethyl)-2,3-dimethylphenoxy]ethyl]-6-ethylpyrimidin-4-amine], abamectin, milbemectin, ivermectin, azadirachtin [AZAD] and polynactins complex including tetranactin, dinactin and trinactin.

Repellents to be used together with the present compounds include deet [N,N-diethyl-m-toluamide], carane-3,4-diol, 1-methylpropyl 2-(2-hydroxyethyl)-1-piperidinecarboxylate, p-menthane-3,8-diol, botanical essential oils having pest repellency, 2,3,4,5-bis(Δ$^2$-butylene)tetrahydro furfural, di-n-propyl isocinchomeronate, di-n-butyl succinate, 2-hydroxyethyl octyl sulfide, and so on.

When the present compound is applied as an active ingredient of pesticides for agricultural use, the amount of application is generally 5 to 500 g per 1000 m$^2$. Emulsifiable concentrates, wettable powders and flowable formulations are diluted with water to the concentration of 0.1 to 1000 ppm. Granules and dusts are not diluted but used as prepared.

When the present compound is applied as an active ingredient of pesticides for house-hold use, sanitary use and animal-health use, emulsifiable concentrates, wettable powders and flowable formulations are diluted with water to the concentration of 0.1 to 10000 ppm. Oil solutions, aerosols, fumigants, volatile agents, fogging agents, ULV formulations, poisonous baits and resin or sheet formulations are used as prepared.

Furthermore, the present compound can be formulated with one or more subliming substances. Such a formulation may be a tablet which can be prepared by solidifying a mixture of the present compound and a subliming substance molten under heating or pressing the mixture under a pressure of 3 to 15 kg/cm$^2$. The amount of the present compound in the tablet is generally 1 to 25% by weight. The subliming substances include 2,4,6-triisopropyl-1,3,5-trioxane, tricyclo[5,5,1,0]decane, acetone oxime, amyl carbamate, butyl carbamate, para-butylaldehyde, chloroacetanilides, 4-chloro-3-methylphenol, cyclohexanone oxime, diacetamide, dihydroxyhexane, dimethyl oxalate, dimethylquinone, furfural oxime, p-dichlorobenzene, naphthalene, camphor and so on. The formulation can volatilize the present compound with the subliming substance at room temperature. Therefore, it is very effective against flying insects such as mosquitoes and flies and fabric pest insects such as casemaking clothes moth, webbing clothes moth and robe beetle. As the above-mentioned subliming substances have insecticidal activity, additive or synergistic effect may be expected.

The amount and concentration of application may be varied optionally according to the type of the formulations, time, place, and method of application, the type of noxious pests and the damage.

The present compounds also have an efficiency as a repellent and can be utilized as an active ingredient of a repellent. When the present compounds are used for repellents, they are preferably formulated to a pest-proof sheet especially cockroach-proof sheet. However, the formulation type of the repellent is not limited and may be formulated to an aerosol formulation, an oil solution, dusts or the like. The present repellent can be used for repelling cockroaches, mosquitoes, flies and so on.

Examples

The invention will be further illustrated in detail by the production examples, formulation examples and biological tests.

Production Example 1

(1RS,cis)-3-(Z-2-chloro-3,3,3-trifluoroprop-1-enyl)-2,2-dimethylcyclopropanecarbonyl chloride (2282 mg) was added under ice-cooling to a mixed solution of 5-methyl-2-furfuryl alcohol (1000 mg), 2,6-di-tert-butyl-4-methylphenol (5 mg), pyridine (1057 mg) and toluene (30 ml) and the mixture was kept at room temperature for 8 hours. The reaction mixture was poured into 5% aqueous solution of citric acid under ice-cooling and extracted three times with diethyl ether. The combined ether layer was washed successively with a saturated sodium bicarbonate solution and a saturated sodium chloride solution, and dried over anhydrous magnesium sulfate. After removal of the solvent under reduced pressure, the obtained residue was subjected to silica gel column chromatography (eluent; n-hexane/ethyl acetate=30/1) to give 2495 mg of 5-methyl-2-furfuryl (1RS,cis)-3-(Z-2-chloro-3,3,3-trifluoroprop-1-enyl)-2,2-dimethylcyclopropanecarboxylate [the present compound (1)]

Yield; 83%; $n_D^{29}$; 1.4681; $^1$H-NMR (internal standard; TMS, in CDCl$_3$) δ values (ppm); 1.28(s, 3H), 1.29(s, 3H), 2.00(d, 1H), 2.16(dd, 1H), 2.31(s, 3H), 5.00(s, 2H), 5.92(d, 1H), 6.28(d, 1H), 6.92(d, 1H).

Production Example 2

(1RS,cis)-3-(Z-2-chloro-3,3,3-trifluoroprop-1-enyl)-2,2-dimethyl-cyclopropanecarbonyl chloride (2070 mg) was added under ice-cooling to a mixed solution of 5-ethyl-2-furfuryl alcohol (1000 mg), 2,6-di-tert-butyl-4-methylphenol (5 mg), pyridine (941 mg) and toluene (30 ml) and the mixture was kept at room temperature for 8 hours. The reaction mixture was poured into 5% aqueous solution of citric acid under ice-cooling and extracted three times with diethyl ether. The combined ether layer was washed successively with a saturated sodium bicarbonate solution and a saturated s odium chloride solution, and dried over anhydrous magnesium sulfate. After removal of the solvent under reduced pressure, the obtained residue was subjected to silica gel column chromatography (eluent; n-hexane/ethyl acetate=30/1) to give 2270 mg of 5-ethyl-2-furfuryl (1RS,cis)-3-(Z-2-chloro-3,3,3-trifluoroprop-1-enyl)-2,2-dimethyl-cyclopropanecarboxylate [the present compound (2)]

Yield; 82%; $n_D^{29}$; 1.4687; $^1$H-NMR (internal standard; TMS, in CDCl$_3$) δ values (ppm); 1.23(t, 3H), 1.29(s, 3H), 1.31(s, 3H), 2.01(d, 1H), 2.18(dd, 1H), 2.66(q, 2H), 5.01(s, 2H), 5.95(d, 1H), 6.30(d, 1H), 6.93(d, 1H).

Production Example 3

(1RS,cis)-3-(Z-2-chloro-3,3,3-trifluoroprop-1-enyl)-2,2-dimethyl-cyclopropanecarbonyl chloride (1303 mg) was added under ice-cooling to a mixed solution of 5-propyl-2-furfuryl alcohol (700 mg), 2,6-di-tert-butyl-4-methylphenol (5 mg), pyridine (592 mg) and toluene (30 ml) and the mixture was kept at room temperature for 8 hours. The reaction mixture was post-treated in the same procedure as production example 1 to give 1350 mg of 5-propyl-2-furfuryl (1RS,cis)-3-(Z-2-chloro-3,3,3-trifluoroprop-1-enyl)-2,2-dimethylcyclopropanecarboxylate [the present compound (3)]

Yield; 74%; $n_D^{29}$; 1.4671; $^1$H-NMR(internal standard; TMS, in CDCl$_3$) δ values (ppm); 0.98(t, 3H), 1.28(s, 3H), 1.29(s, 1H), 1.58–1.78(m, 2H), 2.01(d, 1H), 2.18(dd, 1H), 2.61(t, 2H), 5.02(s, 2H), 5.93(d, 1H), 6.28(d, 1H), 6.95(d, 1H).

Production Example 4

(1RS,cis)-3-(Z-2-chloro-3,3,3-trifluoroprop-1-enyl)-2,2-dimethyl-cyclopropanecarbonyl chloride (28 mg) was added under ice-cooling to a mixed solution of 5-allyl-2-furfuryl alcohol (10 mg), 2,6-di-tert-butyl-4-methylphenol (5 mg), pyridine (13 mg) and toluene (5 ml) and the mixture was kept at room temperature for 8 hours. The reaction mixture was post-treated in the same procedure as production example 1 to give 17 mg of 5-allyl-2-furfuryl (1RS,cis)-3-(Z-2-chloro-3,3,3-trifluoroprop-1-enyl)-2,2-dimethylcyclopropanecarboxylate [the present compound (4)]

Yield; 65%; $n_D^{25}$; 1.4759; $^1$H-NMR (internal standard; TMS, in CDCl$_3$) δ values (ppm); 1.29(s, 3H), 1.30(s, 3H), 2.01(d, 1H), 2.15(dd, 1H), 3.41(d, 2H), 5.01(s, 2H), 5.08–5.21(m, 2H), 5.84–5.97(m, 2H), 5.98(d, 1H), 6.31(d, 1H), 6.91(d, 1H).

Production Examples 5

5-methyl-2-furfuryl (1R,cis)-3-(Z-2-chloro-3,3,3-trifluoroprop-1-enyl)-2,2-dimethylcyclopropanecarboxylate [the present compound (5)] can be produced by using (1R,cis)-3-(Z-2-chloro-3,3,3-trifluoroprop-1-enyl)-2,2-dimethylcyclopropanecarbony chloride in place of (1RS,cis)-3-(Z-2-chloro-3,3,3-trifluoroprop-1-enyl)-2,2-dimethylcyclopropanecarbonyl chloride in production examples 1.

Production Examples 6

5-methyl-2-furfuryl (1R,trans)-3-(Z-2-chloro-3,3,3-trifluoroprop-1-enyl)-2,2-dimethylcyclopropanecarboxylate [the present compound (6)] can be produced by using (1R,trans)-3-(Z-2-chloro-3,3,3-trifluoroprop-1-enyl)-2,2-dimethylcyclopropanecarbony chloride in place of (1RS,cis)-3-(Z-2-chloro-3,3,3-trifluoroprop-1-enyl)-2,2-dimethylcyclopropanecarbonyl chloride in production examples 1.

Production Examples 7–9

5-ethyl-2-furfuryl (1R,cis)-3-(Z-2-chloro-3,3,3-trifluoroprop-1-enyl)-2,2-dimethylcyclopropanecarboxylate [the present compound (7)], 5-propyl-2-furfuryl (1R,cis)-3-(Z-2-chloro-3,3,3-trifluoroprop-1-enyl)-2,2-dimethylcyclopropanecarboxylate [the present compound (8)] and 5-allyl-2-furfuryl (1R,cis)-3-(Z-2-chloro-3,3,3-trifluoroprop-1-enyl)-2,2-dimethylcyclopropanecarboxylate [the present compound (9)] can be produced by using (1R,cis)-3-(Z-2-chloro-3,3,3-trifluoroprop-1-enyl)-2,2-dimethylcyclopropanecarbony chloride in place of (1RS,cis)-3-(Z-2-chloro-3,3,3-trifluoroprop-1-enyl)-2,2-dimethylcyclopropanecarbonyl chloride in production examples 4–6.

Production Examples 10–12

5-ethyl-2-furfuryl (1R,trans)-3-(Z-2-chloro-3,3,3-trifluoroprop-1-enyl)-2,2-dimethylcyclopropanecarboxylate [the present compound (10)], 5-propyl-2-furfuryl (1R,trans)-3-(Z-2-chloro-3,3,3-trifluoroprop-1-enyl)-2,2-dimethylcyclopropanecarboxylate [the present compound (11)] and 5-allyl-2-furfuryl (1R,trans)-3-(Z-2-chloro-3,3,3-trifluoroprop-1-enyl)-2,2-dimethylcyclopropanecarboxylate [the present compound (12)] can be produced by using (1R,trans)-3-(Z-2-chloro-3,3,3-trifluoroprop-1-enyl)-2,2-dimethylcyclopropanecarbony chloride in place of (1RS,cis)-3-(Z-2-chloro-3,3,3-trifluoroprop-1-enyl)-2,2-dimethylcyclopropanecarbonyl chloride in production examples 4–6.

The alcohol compounds represented by the formula (II) used in the above production examples can be prepared according to the following example.

Preparation of 5-methyl-2-furfuryl alcohol:

Sodium borohydride (515 mg) was added to a mixture of 5-methylfurfural (3 g) and methanol (30 ml) under ice-cooling and the mixture was stirred for 1 hour. The reaction mixture was poured into 5% aqueous solution of citric acid under ice-cooling and extracted two times with diethyl ether. The combined ether layer was washed successively with a saturated sodium bicarbonate solution and a saturated sodium chloride solution, and dried over anhydrous magnesium sulfate. After removal of the solvent under reduced pressure, the obtained residue was subjected to silica gel column chromatography to give 2.3 g of 5-methyl-2-furfuryl alcohol.

Yield; 75%; $^1$H-NMR (internal standard; TMS, in $CDCl_3$) δ values (ppm); 1.71(t, 1H), 2.31(d, 3H), 4.53(d, 2H), 5.96(d, 1H), 6.17(d, 1H)

Preparation of 5-ethyl-2-furfuryl alcohol:

Under an atmosphere of nitrogen, n-hexane solution of n-butyllithium (1.69 M, 69.5 ml) was added to a mixture of furfuryl alcohol (5 g) and tetrahydrofuran (75 ml) at −78° C. and the mixture was stirred for 1 hour. After ethyl iodide (9.6 g) was added to the mixture, the mixture was allowed to be at room temperature and stirred for 8 hours. The reaction mixture was poured into 5% aqueous solution of citric acid under ice-cooling and extracted two times with diethyl ether. The combined ether layer was washed successively with a saturated sodium bicarbonate solution and a saturated sodium chloride solution, and dried over anhydrous magnesium sulfate. After removal of the solvent under reduced pressure, the obtained residue was subjected to silica gel column chromatography to give 1.2 g of 5-ethyl-2-furfuryl alcohol.

$^1$H-NMR (internal standard; TMS, in $CDCl_3$) δ values (ppm); 1.22(t, 3H), 1.72(t, 1H), 2.62(q, 2H), 4.56(d, 2H), 5.91(d, 1H), 6.19(d, 1H).

Preparation of 5-propyl-2-furfuryl alcohol:

Under an atmosphere of nitrogen, n-hexane solution of n-butyllithium (1.69 M, 70 ml) was added to a mixture of furfuryl alcohol (5 g) and tetrahydrofuran (75 ml) at −78° C. and the mixture was stirred for 1 hour. After propyl iodide (10.4 g) was added to the mixture, the mixture was allowed to be at room temperature and stirred for 8 hours. The reaction mixture was post-treated in the same procedure as the above preparation to give 1.2 g of 5-propyl-2-furfuryl alcohol.

$^1$H-NMR (internal standard; TMS, in $CDCl_3$) δ values (ppm); 0.98(t, 3H), 1.53–1.72(m, 2H), 1.82(br, 1H), 2.58(t, 2H), 4.52(br, 2H), 5.40(d,1H), 6.15(d, 1H).

Preparation of 5-allyl-2-furfuryl alcohol:

Under an atmosphere of nitrogen, n-hexane solution of n-butyllithium (1.69 M, 70 ml) was added to a mixture of furfuryl alcohol (5 g) and tetrahydrofuran (75 ml) at −78° C. and the mixture was stirred for 1 hour. After allyl iodide (10.3 g) was added to the mixture, the mixture was allowed to be at room temperature and stirred for 8 hours. The reaction mixture was post-treated in the same procedure as the above preparation to give 0.87 g of 5-allyl-2-furfuryl alcohol.

$^1$H-NMR (internal standard; TMS, in $CDCl_3$) δ values (ppm); 1.72(br, 1H), 3.40(d, 2H), 4.52(d, 2H), 4.92–5.25(m, 2H), 5.65–5.98(m, 1H), 5.98(d,1H), 6.19(d, 1H).

Formulation examples are described below. Parts represent parts by weight in the following examples.

Formulation Example 1; Emulusifiable Concentrates

Twenty parts of each of the present compound (1) to (12) are dissolves in 65 parts of xylene, mixed with 5 parts of Sorpol 3005X (surfactant provided by Toho Chemical Co., Ltd.), and stirred sufficiently to give 20% emulusifiable concentrates for each compound.

Formulation Example 2; Wettable Powders

Forty parts of each of the present compound (1) to (12) are mixed first with 5 parts of Sorpol 3005X and then with 32 parts of Carplex #80 (fine powder of synthetic hydrated silicon oxide provided by Shionogi & Co., Ltd.) and 23 parts of 300-mesh diatomaceous earth, and stirred with a blender to give 40% wettable powders for each compound.

Formulation Example 3; Granules 1.5 parts of each of the present compound (1) to (12) are mixed with 98.5 parts of AGSORB LVM-MS 24/48 (granular carrier of calcined monmorillonite having the particle diameter of 24 to 48 meshes provided by OIL DRI Corp.) sufficiently to give 1.5% granules for each compound.

Formulation Example 4; Microcapsules

A mixture of 10 parts of each of the present compound (1) to (12), 10 parts of phenylxylylethane and 0.5 part of Sumidur L-75 (tolylenediisocyanate provided by Sumitomo Bayer Urethane Co., Ltd.) is added to 20 parts of a 10% aqueous solution of gum arabic, and stirred with a homomixer to give an emulsion having the mean particle diameter of 20 μm. The emulsion is further mixed with 2 parts of ethylene glycol and allowed to react on a water bath of 60° C. for 24 hours to give a microcapsule slurry.

A thicking agent is prepared by dispersing 0.2 part of xanthan gum and 1.0 part of Beagum R (aluminum magnesium silicate provided by Sansyo Co., Ltd.) in 56.3 parts of ion-exchanged water.

42.5 parts of the above microcapsule slurry and 57.5 parts of the above thicking agent are mixed to give 10% microencapsulated formulations for each compound.

Formulation Example 5; Flowable Formulations

A mixture of 10 parts of each of the present compound (1) to (12) and 10 parts of phenylxylylethane is added to 20 parts of a 10% aqueous solution of polyethylene glycol and stirred with a homomixer to give an emulsion having the mean particle diameter of 3 μm.

A thicking agent is prepared by dispersing 0.2 part of xanthan gum and 1.0 part of Beagum R in 58.8 parts of ion-exchanged water.

Forty parts of the above emulsion and 60 parts of the above thicking agent are mixed to give 10% flowable formulations for each compound.

Formulation Example 6; Dusts

Five parts of each of the present compound (1) to (12) are mixed with 3 parts of Carplex #80, 0.3 parts of PAP and 91.7 parts of 300-mesh talc, and stirred with a blender to give 5% dusts for each compound.

Formulation Example 7; Oil Solutions 0.1 part of each of the present compound (1) to (12) is dissolved in 5 parts of dichloromethane and mixed with 94.9 parts of deodorized kerosine to give 0.1% oil solutions for each compound.

Formulation Example 8; Oil-based Aerosols

An aerosol vessel is filled with the solution obtained by dissolving 1 part of each of the present compound (1) to (12)

with 5 parts of dichloromethane and 34 parts of deodorized kerosine. The vessel is then equipped with a valve and 60 parts of propellant (liquefied petroleum gas) is charged through the valve into the aerosol vessel under pressure to give oil-based aerosols for each compound.

Formulation Example 9; Water-based Aerosols

An aerosol vessel is filled with 50 parts of ion-exchanged water and a mixture of 0.6 part of each of the present compound (1) to (12), 5 parts of xylene, 3.4 parts of deodorized kerosine and 1 part of Atmos 300 (emulsifier provided by Atlas Chemical Co.). The vessel is then equipped with a valve and 40 parts of propellant (liquefied petroleum gas) is charged through a valve into the aerosol vessel under pressure to give water-based aerosols for each compound.

Formulation Example 10; Mosquito-coils

A solution prepared by dissolving 0.3 g of each of the present compound (1) to (12) in 20 ml of acetone is homogeneously mixed with 99.7 g of a carrier for a mosquito-coil (mixture of Tabu powder, Pyrethrum marc and wood powder at the ratio of 4:3:3). After 120 ml of water is added, the mixture is kneaded sufficiently, molded and dried to give mosquito-coils for each compound.

Formulation Example 11; Mosquito-mats For Electric Heating Fumigation 10 ml of solution is prepared by dissolving 0.8 g of each of the present compound (1) to (12) and 0.4 g of piperonyl butoxide in acetone. 0.5 ml of the obtained solution is impregnated a base material (a plate of compacted fibrils of a mixture of pulp and cotton linters: 2.5 cm×1.5 cm×0.3 cm) homogeneously to give mosquito-mats for each compound.

Formulation Example 12; Solutions For Electric Heating Fumigation

Three parts of each of the present compound (1) to (12) is dissolved in 97 parts of deodorized kerosine. The obtained solution is charged in a vessel of polyvinyl chloride. In the vessel is inserted a porous absorptive wick which is inorganic powder solidified with a binder and then calcined, the upper portion of which wick can be heated with a heater, to give electric heating fumigation devices using a liquid for each compound.

Formulation Example 13; Fumigants

A solution prepared by dissolving 100 mg of each of the present compound (1) to (12) in an appropriate amount of acetone is impregnated a porous ceramic plate (4.0 cm×4.0 cm×1.2 cm) to give fumigants for each compound.

Formulation Example 14; Volatile Agents

A solution prepared by dissolving 100 $\mu$g of each of the present compound (1) to (12) in an appropriate amount of acetone is applied onto filter paper (2.0 cm×2.0 cm×0.3 mm) and the acetone is evaporated to give volatile agents for each compound.

Formulation Example 15; Acaricidal Sheets

An acetone solution containing each of the present compound (1) to (12) is impregnated filter paper so that the concentration of each of the present compound is 1 g /1 m$^2$ and the acetone is evaporated to give acaricidal sheets for each compound.

Formulation Example 16; Tablets

Each of the present compound (1) to (12) (0.1 g) and p-dichlorobenzene (1.1 g) molten under heating are mixed, poured into a mold and solidified to give tablets for each compound.

The present compounds were respectively tested as an active ingredient of a pesticide. In the description below, the compounds used as references (racemic compounds) are shown by the symbols in Table 1.

TABLE 1

| Symbols | Chemical Structures | Remarks |
| --- | --- | --- |
| A | 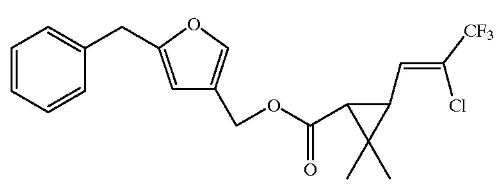 | A compound described in EP-3336-A |
| B | 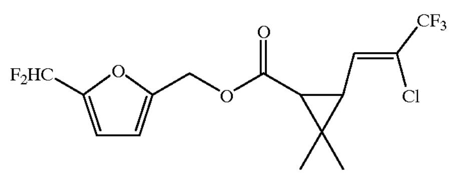 | A compound described in USP-5405865 |

TABLE 1-continued

| Symbols | Chemical Structures | Remarks |
|---|---|---|
| C | 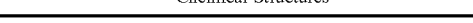 | A compound described in JP-Hei6-211611-A |

Biological Test 1

Emulsifiable concentrates were prepared for each of the present compounds according to the formulation example 1. Thirteen grams of artificial bait for tobacco cutworm (*Spodoptera litura*) were placed in a polyethylene cup (diameter: 11 cm) and impregnated with 2 ml of the 500 ppm emulsion prepared by diluting the emulsifiable concentrates with water. Ten 4-instar larvae of *Spodoptera litura* were put in the polyethylene cup. After 6 days, the mortality of the larvae was examined. As a result, it was found that the present compounds (1), (2), (3) and (4) exhibited the mortality of 100%.

Biological Test 2

A stalk of a rice plant was dipped for one minute in a 500 ppm aqueous emulsion obtained by diluting each emulsifiable concentrate of the present compounds prepared according to the formulation example 1. The rice plant stalk was air-dried and placed in a polyethylene cup (diameter: 5.5 cm) where filter paper (diameter: 5.5 cm) impregnated with 1 ml of water was put. Approximately 30 larvae of brown planthopper (*Nilaparvata lugens*) were put in the polyethylene cup. After 6 days, the mortality of the larvae was examined. As a result, it was found that the present compounds (1), (2), (3) and (4) exhibited the mortality of 90% or more.

Biological Test 3

Filter paper of 5.5 cm in diameter was laid in the bottom of a polyethylene cup (diameter: 5.5 cm). After 1 ml of a 50 ppm aqueous emulsion obtained by diluting each emulsifiable concentrate of the present compound (1) prepared according to the formulation example 1 was dropped on the filter paper and approximately 30 eggs of southern corn rootworm (*Diabrotica undecimpunctata howardi*) and one sprouting corn crop as bait were placed in the polyethylene cup. After 8 days, the mortality of the hatched larvae and eggs was examined. As a result, it was found that the present compounds (1), (2), (3) and (4) exhibited the mortality of 100%.

Biological Test 4

Filter paper of 5.5 cm in diameter was laid in the bottom of a polyethylene cup (diameter: 5.5 cm). After 0.7 ml of a 500 ppm aqueous emulsion obtained by diluting each emulsifiable concentrate prepared according to the formulation example 1 was dropped on the filter paper and approximately 30 mg of sucrose as bait was uniformly scattered. Ten female houseflies (*Musca domestica*), which were low sensitive to pyrethroids, were left in the cup with a cover. After one day, the mortality was examined. As a result, it was found that the present compounds (1), (2), (3) and (4) exhibited the mortality of 100%.

Biological Test 5

Filter paper of 5.5 cm in diameter was laid in the bottom of a polyethylene cup (diameter: 5.5 cm). After 0.7 ml of a 500 ppm aqueous emulsion obtained by diluting each emulsifiable concentrate prepared according to the formulation example 1 was dropped on the filter paper and approximately 30 mg of sucrose as bait was uniformly scattered. Two male German cockroaches (*Blattella germanica*), which were low sensitive to pyrethroids, were left in the cup with a cover. After six days, the mortality was examined. As a result, it was found that the present compounds (1), (2), (3) and (4) exhibited the mortality of 100%.

Biological Test 6

0.7 ml of aqueous emulsion, obtained by diluting emulsifiable concentrate prepared for each of the present compounds according to the formulation example 1, was added to 100 ml of ion-exchanged water (concentration of active ingredient: 3.5 ppm). Twenty last-instar larvae of common mosquitoes (*Culex pipiens pallens*) were left in the water. After one day, the mortality of the common mosquitoes was examined. As a result, it was found that the present compounds (1), (2), (3) and (4) exhibited the mortality of 90% or more.

Biological Test 7

Ten female common mosquitoes (*Culex pipiens pallens*) were left in a glass chamber (70 cm×70 cm×70 cm: 0.34 $m^3$). 0.7 ml of 0.1% oil solution prepared for each of the present compounds according to the formulation example 7 was sprayed with a spray gun at 0.8 atmospheric pressure. After 15 minutes, the rate of knocked-down mosquitoes was examined. As a result, it was found that the present compounds (1), (2), (3) and (4) exhibited the rate of knocked-down mosquitoes of 90% or more.

Biological Test 8

Mosquito-coil containing the present compound in an amount of 0.3% was prepared according to the formulation example 10 for the present compounds. Ten female common mosquitoes (*Culex pipiens pallens*) were left in a glass chamber (70 cm×70 cm×70 cm: 0.34 $m^3$) and 1.0 g of 0.3% mosquito-coil having both ends lit was placed in the glass chamber. After 15 minutes, the rate of knocked-down mosquitoes was examined. As a result, it was found that the present compounds (1), (2), (3) and (4) exhibited the rate of knocked-down mosquitoes of 100%.

Biological Test 9

An acetone solution for each of the present compounds was applied to 10 female houseflies (*Musca domestica*) at the back thoracic region (active ingredient: 5 µg/one housefly) and the houseflies were left with water and feed. After 24 hours, the percent moribund was examined (two replicate). As a result, it was found that the present compounds (1), (2), (3) and (4) exhibited the percent moribund of 100%.

Biological Test 10

After 0.64 ml of a 0.05 (w/v) % acetone solution of the present compounds was dropped into an aluminum plate (bottom diameter: 7 cm), acetone was air-dried. Ten female houseflies (*Musca domestica*) were left in a polyethylene cup (diameter: 9 cm; depth: 4.5 cm) and the cup was sealed with a 16-mesh nylon net to prevent direct contact of the houseflies with the compound. The cup was placed upside down on the aluminum plate at 25° C. for 120 minutes. The cup was then removed from the aluminum plate, and water and feed were given to the houseflies. After 24 hours, the percent moribund was examined (two replicate). As a result, it was found that the present compounds (1), (2), (3) and (4) exhibited the percent moribund of 100%.

Biological Test 11

After 0.64 ml of a 0.05 (w/v) % acetone solution of the present compounds was dropped into an aluminum plate (bottom diameter: 7 cm), acetone was air-dried. Ten female common mosquitoes (*Culex pipiens pallens*) were left in a polyethylene cup (diameter: 9 cm; depth: 4.5 cm) and the cup was sealed with a 16-mesh nylon net to prevent direct contact of the mosquitoes with the compound. The cup was placed upside down on the aluminum plate at 25° C. for 120 minutes. The cup was then removed from the aluminum plate, and water and feed were given to the mosquitoes. After 24 hours, the mortality was examined (two replicate). As a result, it was found that the present compounds (1), (2), (3) and (4) exhibited the mortality of 100%.

Biological Test 12

Each of the present compounds diluted with acetone to a predetermined concentration was applied to ten middle instar larvae of webbing clothes moth (*Tineola bisselliella*) at the central part of the back so as to give the active ingredient in a dose of 3 μg/insect. A wool muslin fabric (2 cm×2 cm in size) was given to the webbing clothes moths as the food. After 7 days, the mortality and the degree of damage of the wool muslin fabric by the moths were examined (two replicate). As a result, it was found that the present compounds (1), (2), (3) and (4) exhibited the mortality of 100% and no damage. In contrast, a group of the moths treated with acetone containing no active ingredient showed a mortality of 0% and severe damage.

Biological Test 13

A wool muslin fabric (2 cm×2 cm in size) was placed on the bottom of a polyethylene cup (bottom diameter: 10 cm, opening part diameter: 12.5 cm, height: 9.5 cm, volume: 950 cm$^3$). Ten middle instar larvae of webbing clothes moth (*Tineola bisselliella*) were put in the cup and each of the volatile agents prepared according to the formulation example 14 was hung from the cap in the interior of the cup. After standing at 25° C. for 1 week, the cup was opened, and the mortality and the degree of damage of the wool muslin fabric by the moths were examined (two replicate). As a result, it was found that the present compounds (1), (2), (3) and (4) exhibited the mortality of 100% and no damage.

Biological Test 14

A filter paper (3.2 cm×3.2 cm in size) treated with 36 mg of each of the present compounds and two wool muslin fabrics (25 cm×25 cm in size) were hung down at the upper part of a corrugated cardboard box (29 cm×29 cm×29 cm in size). After standing at 25° C. and a humidity of 60% for 1 week, two tea-strainer balls holding 7 to 10 middle instar larvae of webbing clothes moth (*Tineola bisselliella*) and one piece of wool muslin cloth (2 cm×2 cm in size) were hung down at the upper part of the box. The box was closed with a lid. After one week, the box was opened, and the percent moribund and the degree of damage of the wool muslin cloth by the moths were examined. The same tests was repeated 2 weeks, 3 weeks and 5 weeks after the treatment to examine the persistance of the present compound. The results are shown in Table 2. The degree of damage was represented by "−" in no damage, "+" in slight damage, "++" in heavy damage and "+++" in severe damage.

TABLE 2

| com- | percent moribund degree of damage | | | |
|---|---|---|---|---|
| pound | After 1 week | After 2 weeks | After 3 weeks | After 5 weeks |
| (1) | 100 − | 100 − | 100 − | 100 − |
| (2) | 100 − | 100 − | 100 − | 100 − |
| (3) | 100 − | 100 − | 100 − | 100 − |
| (4) | 100 − | 100 − | 100 − | 100 − |
| A | 0 +++ | 0 +++ | 5 +++ | 5 +++ |
| B | 50 +++ | 33 +++ | 53 +++ | 42 +++ |
| C | 7 +++ | 63 +++ | 20 +++ | 37 +++ |
| No treatment | 0 +++ | 0 +++ | 0 +++ | 0 +++ |

Biological Test 15 (Repellency)

On a filter paper (6 cm×9 cm), 1.0 ml of an acetone solution (0.1% by weight) of the present compound (1) was spread and then dried to afford a sheet formulation for repelling cockroaches. The obtained sheet was folded as to be a triangular tube where one side of the triangle-shaped base was 3 cm.

In a plastic cup (650 ml volume), said triangular tube was placed as a shelter (cockroach hiding residence). Ten adult German cockroaches (*Blattela germanica*) were placed in said plastic cup together with food and water and then observed the number of cockroaches in the shelter 24 hours later (two replicate). Repellency (%) was calculated by the following formula:

$$\text{Repellency}(\%) = \frac{\text{Total No. of cockroaches} - \text{No. of cockroaches inside shelter}}{\text{Total No. of cockroaches}} \times 100$$

The results are given in table 3.

TABLE 3

| | Repellency (%) |
|---|---|
| Compound (1) | 100 |
| No treatment | 5 |

Biological Test 16

A designated amount of piperonyl butoxide was added to the present compound (1) as shown in Table 4. The combination rate of piperonyl butoxide to the present compound was 0, 2, 4, 8 and 16 times. The mixture was dissolved in acetone. The acetone solution (0.5 μL) was applied to 10 female houseflies (*Musca domestica*) at the back thoracic region. After 24 hours, the number of dead insects was observed (2 repetition) and mortality was calculated. The results were shown below.

TABLE 4

| Treated amount (μg(female)) | | Mortality |
|---|---|---|
| Present compound (1) | Piperonyl butoxide | (%) |
| 0.5 | 0 | 30 |
| 0.5 | 1.0 | 95 |
| 0.5 | 2.0 | 100 |

TABLE 4-continued

| Treated amount (μg(female)) | | Mortality |
|---|---|---|
| Present compound (1) | Piperonyl butoxide | (%) |
| 0.5 | 4.0 | 100 |
| 0.5 | 8.0 | 100 |
| 0 | 8.0 | 0 |
| Untreated | | 5 |

Biological Test 17

A designated amount of piperonyl butoxide was added to the present compound (2) as shown in Table 5. The combination rate of piperonyl butoxide to the present compound was 0, 2, 4, 8 and 16 times. The mixture was dissolved in acetone. The acetone solution (0.5 μL) was applied to 10 female houseflies (*Musca domestica*) at the back thoracic region. After 24 hours, the number of dead insects was observed (2 repetition) and mortality was calculated. The results were shown below.

TABLE 5

| Treated amount (μg/female) | | Mortality |
|---|---|---|
| Present compound (2) | Piperonyl butoxide | (%) |
| 0.2 | 0 | 30 |
| 0.2 | 0.4 | 85 |
| 0.2 | 0.8 | 100 |
| 0.2 | 1.6 | 100 |
| 0.2 | 3.2 | 100 |
| 0 | 8.0 | 0 |
| Untreated | | 0 |

Stability Test

Each of the present compounds (3.3 mg) was dissolved in acetone, and the resulting acetone solution was impregnated into a filter paper (2 cm×1.5 cm in size) and air-dried. Separately from this, a filter paper treated with a brass powder [a filter paper, 5.5 cm in diameter, into one surface of which about 0.03 mg/cm$^2$ of a brass powder (Cu/Zn= 76–78/22–24) has been rubbed] was folded in two with the brass powder-treated surface turned inwards. The above chemical-treated filter paper was held between two halves of the folded filter paper, fixed thereto with a clip and put in an aluminum-laminated bag. This bag was tightly closed by heat-sealing and kept in a constant-temperature vessel, at 60° C. for 48 hours. Thereafter. the bag was opened, and the color change and offensive odor of the brass powder-treated filter paper were examined. As a result, no clear offensive odor nor color change was observed in any of the present compounds (1) to (4).

A color change on portions of clothing which are ornamented with copper or dyed with copper-containing dyes or an offensive odor is sometimes observed due to a kind of pyrethroid compounds under severe conditions. The above test shows that the present compound has no offensive odor nor color change even under severe conditions.

Toxicity Test

The present compound (1) was diluted with corn oil to an appropriate concentration. After subjecting the rats to a twenty-hour fasting, 0.1 ml of the diluted solution per 10 g weight was forcibly applied into the stomach of four male 7-week old rats. The rats were given food and water four hours after the application and thereafter regularly fed and watered, and kept in a cage. After 7 days, the mortality was examined for the rats and LD$_{50}$ was calculated. The results are shown in Table 6.

TABLE 6

| compound | LD$_{50}$ (mg/kg) |
|---|---|
| (1) | 300 |
| A | less than 50 |
| B | less than 300 |
| | more than 100 |
| C | less than 100 |

The present compounds have an excellent effect for controlling noxious pests and especially the present compound wherein R is a methyl group has an excellent pesticidal activity and low toxicity.

What is claimed is:

1. An ester compound represented by the following formula (I)

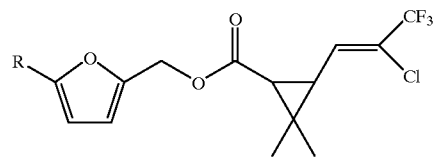

wherein R is a methyl, ethyl, n-propyl or allyl group.

2. The ester compound according to claim 1, wherein R is a methyl group.

3. The ester compound according to claim 1, wherein R is an ethyl group.

4. The ester compound according to claim 1, wherein R is an n-propyl group.

5. The ester compound according to claim 1, wherein R is an allyl group.

6. A pesticidal composition which comprises an ester compound according to claim 1 as an active ingredient, and a carrier.

7. The pesticidal composition according to claim 6, wherein R is a methyl group.

8. A pesticidal composition which comprises an ester compound according to claim 1 as an active ingredient, and at least one subliming substance.

9. The pesticidal composition according to claim 8, wherein the subliming substance is at least one selected from the group consisting of 2,4,6-triisopropyl-1,3,5-trioxane, tricyclo[5,5,1,0]decane, acetone oxime, amyl carbamate, butyl carbamate, para-butylaldehyde, chloroacetanilides, 4-chloro-3-methylphenol, cyclohexanone oxime, diacetamide, dihydroxyhexane, dimethyl oxalate, dimethylquinone, furfural oxime, p-dichlorobenzene, naphthalene and camphor.

10. A pesticidal composition which comprises an ester compound according to claim 1 as an active ingredient, at least one synergist and a carrier.

11. The pesticidal composition according to claim 10, wherein the synergist is at least one selected from the group consisting of piperonyl butoxide, N-(2-ethylhexyl)bicyclo [2.2.1]hept-5-ene-2,3-dicarboximide, N-(2-ethylhexyl)-1-isopropyl-4-methylbicyclo[2.2.1]oct-5-ene-2,3-dicarboximide and 1,1'-oxybis (2,3,3,3-tetrachloropropane).

12. The pesticidal composition according to claim 10, wherein the synergist is piperonyl butoxide.

13. The pesticidal composition according to claim 12, wherein the ratio of the ester compound represented by the following formula (I)

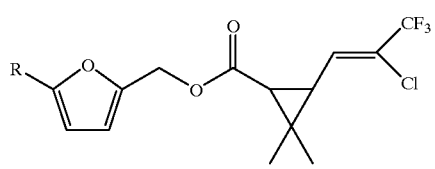
wherein R is a methyl, ethyl, n-propyl or allyl group, to piperonyl butoxide is in a range of 1:1 to 1:20.
14. A method for controlling pests which comprises applying an ester compound according to claim 1 to the pest or their habitats.
15. The method for controlling pests according to claim 14, wherein R is a methyl group.
* * * * *